United States Patent
Lai (10) Patent No.: US 10,874,298 B2
(45) Date of Patent: Dec. 29, 2020

(54) INTRASTROMAL SURGERY CORRECTING LOW ORDER AND HIGH ORDER ABERRATIONS OF THE EYE

(71) Applicant: Shui T. Lai, Windermere, FL (US)

(72) Inventor: Shui T. Lai, Windermere, FL (US)

(*) Notice: Subject to any disclaimer, the term of this patent is extended or adjusted under 35 U.S.C. 154(b) by 161 days.

(21) Appl. No.: 15/967,315

(22) Filed: Apr. 30, 2018

(65) Prior Publication Data

US 2018/0344151 A1    Dec. 6, 2018

Related U.S. Application Data

(63) Continuation of application No. 11/829,027, filed on Jul. 26, 2007, now Pat. No. 9,955,867.

(Continued)

(51) Int. Cl.
*A61F 9/008* (2006.01)
*A61B 3/107* (2006.01)

(52) U.S. Cl.
CPC .......... *A61B 3/107* (2013.01); *A61F 9/00829* (2013.01); *A61F 2009/0088* (2013.01);
(Continued)

(58) Field of Classification Search
CPC .. A61F 9/008; A61F 9/00802; A61F 9/00804; A61F 9/00806; A61F 9/00825;
(Continued)

(56) References Cited

U.S. PATENT DOCUMENTS 5,260,727 A    11/1993    Oksman et al.
5,332,802 A     7/1994    Kelman et al.
(Continued)

FOREIGN PATENT DOCUMENTS

EP    2520220 A1    11/2012
EP    2056755 B1     2/2018
(Continued)

OTHER PUBLICATIONS

PCT Transmittal of International Preliminary Report on Patentability (Chapter I of the Patent Cooperation Treaty), for PCT Application No. PCT/US2007/074522, dated Feb. 5, 2009, 5 pages.
(Continued)

*Primary Examiner* — Ahmed M Farah
(74) *Attorney, Agent, or Firm* — SF Bay Area Patents, LLC; Andrew V. Smith (57) ABSTRACT

A method of correcting wavefront aberrations of an eye includes determining a high precision conventional intrastromal corneal ablation profile based on a direct removal of the intrastromal corneal tissue. An expanded ablation volume profile is constructed based on the direct tissue removal profile and the expanded tissue volume is to be ablated instead to correct to the wavefront aberrations. The thickness of the ablated profile of a conventional ablation profile is expanded by an expansion factor $(N_c-1)/(N_m-N_c)$, $N_c$ is the index of refraction of the cornea and $N_m$ the index of fill material. An expanded ablation volume filled with the fill material produces the effect of correcting wavefront aberrations as if a much smaller tissue volume were ablated without the fill material.

12 Claims, 7 Drawing Sheets

Related U.S. Application Data (60) Provisional application No. 60/820,483, filed on Jul. 26, 2006.

(52) U.S. Cl.
CPC ............... *A61F 2009/00872* (2013.01); *A61F 2009/00897* (2013.01)

(58) Field of Classification Search
CPC .............. A61F 9/00827; A61F 9/00829; A61F 2009/00842; A61F 2009/00872; A61F 2009/00888; A61F 2009/008882; A61F 2009/00897; A61B 3/10; A61B 3/1005; A61B 3/1015; A61B 3/103; A61B 3/107
USPC ............ 606/4, 5, 10–12; 351/205, 206, 212; 128/898
See application file for complete search history.

(56) References Cited

U.S. PATENT DOCUMENTS

| | | | |
|---|---|---|---|
| 5,512,965 A | 4/1996 | Snook | |
| 5,549,632 A | 8/1996 | Lai | |
| 5,786,883 A | 7/1998 | Miller et al. | |
| 5,895,422 A | 4/1999 | Hauber | |
| 5,905,561 A | 5/1999 | Lee et al. | |
| 5,949,521 A | 9/1999 | Williams et al. | |
| 5,984,916 A | 11/1999 | Lai | |
| 5,993,438 A | 11/1999 | Juhasz et al. | |
| 6,110,166 A | 8/2000 | Juhasz | |
| 6,280,470 B1 | 8/2001 | Peyman | |
| 6,325,792 B1 | 12/2001 | Swinger et al. | |
| 6,554,425 B1 | 4/2003 | Roffman et al. | |
| 6,676,653 B2 | 1/2004 | Juhasz et al. | |
| 6,761,454 B2 | 7/2004 | Lai et al. | |
| 6,786,602 B2 | 9/2004 | Abitbol | |
| 6,808,265 B2 | 10/2004 | Cox | |
| 6,836,371 B2 | 12/2004 | Lai et al. | |
| 6,989,008 B2 | 1/2006 | Peyman | |
| 7,217,375 B2 | 5/2007 | Lai | |
| 7,220,255 B2 | 5/2007 | Lai | |
| 7,286,295 B1 | 10/2007 | Sweatt et al. | |
| 7,628,810 B2 | 12/2009 | Christie et al. | |
| 7,699,471 B2 | 4/2010 | Lai | |
| 7,726,811 B2 | 6/2010 | Lai | |
| 7,748,844 B2 | 7/2010 | Lai | |
| 7,959,284 B2 | 6/2011 | Lai | |
| 8,262,220 B2 | 9/2012 | Lai | |
| 8,366,274 B2 | 2/2013 | Lai | |
| 8,409,177 B1 * | 4/2013 | Lai | A61F 9/008 606/4 |
| 9,095,414 B2 * | 8/2015 | Jester | A61F 9/00802 |
| 9,474,647 B2 * | 10/2016 | Bischoff | A61B 34/10 |
| 9,955,867 B2 * | 5/2018 | Lai | A61B 3/107 |
| 2003/0208190 A1 * | 11/2003 | Roberts | A61F 9/008 606/5 |
| 2004/0100619 A1 | 5/2004 | Olivier et al. | |
| 2004/0160576 A1 | 8/2004 | Lai et al. | |
| 2004/0246440 A1 | 12/2004 | Andino et al. | |
| 2005/0157256 A1 | 7/2005 | Gotou et al. | |
| 2005/0182488 A1 | 8/2005 | Peyman | |
| 2005/0213040 A1 | 9/2005 | Gross et al. | |
| 2005/0259221 A1 | 11/2005 | Marmo | |
| 2005/0270491 A1 | 12/2005 | Dai et al. | |
| 2006/0007397 A1 | 1/2006 | Lai | |
| 2006/0017990 A1 | 1/2006 | Platt et al. | |
| 2006/0052547 A1 | 3/2006 | Jethmalani et al. | |
| 2007/0081126 A1 | 4/2007 | Blum et al. | |
| 2007/0195264 A1 | 8/2007 | Lai | |
| 2007/0258046 A1 | 11/2007 | Lai | |
| 2007/0291224 A1 | 12/2007 | Lai | |
| 2008/0212024 A1 | 9/2008 | Lai | |

FOREIGN PATENT DOCUMENTS

| | | | |
|---|---|---|---|
| EP | 2026693 B1 | 7/2019 | |
| WO | 2005/116729 A2 | 12/2005 | |
| WO | 2006/015490 A1 | 2/2006 | |
| WO | 2006/023404 A2 | 3/2006 | |
| WO | 2008/014419 A2 | 1/2008 | |
| WO | 2008/036695 A2 | 3/2008 | |
| WO | 2008/036695 A3 | 7/2008 | |
| WO | 2008/014419 A3 | 11/2008 | |

OTHER PUBLICATIONS

PCT Notification of Transmittal of the International Search Report and the Written Opinion of the International Searching Authority, or the Declaration, for PCT Application No. PCT/US2007/074522, paper dated Sep. 11, 2008, 6 pages.

\* cited by examiner

INTRASTROMAL SURGERY CORRECTING LOW ORDER AND HIGH ORDER ABERRATIONS OF THE EYE

PRIORITY

This application is a Continuation of U.S. patent application Ser. No. 11/829,027, filed Jul. 26, 2007, now U.S. Pat. No. 9,955,867; which claims the benefit of priority to U.S. provisional patent application No. 60/820,483, filed Jul. 26, 2006, each of which is hereby incorporated by reference.

BACKGROUND

Currently refractive errors are routinely corrected with a laser surgical procedure LASIK or PRK. Laser energy is applied to the front surface of the eye in PRK, or to the stromal surface after a thin corneal flap is resected and pulled back in LASIK. Both procedures have disadvantages. In PRK, it is painful and the healing time is long. In LASIK, it is less painful. However, the corneal flap being cut weakens the mechanical structure of the eye. Reported cases of post-LASIK ectasia have begun to cause concerns and serious discussions regarding its prevention have sprung up at recent ophthalmology meetings. The focus of the discussions is on patient selection, and when to avoid operating on patients with "risk factors".

Therefore, it is desirable to provide a surgical correction method that does not cause ectasia, improves healing time, and results in less post-operative pain.

SUMMARY OF THE INVENTION

A method is provided for correcting wavefront aberrations of an eye. A corneal ablation tissue volume profile is determined for an eye in three dimensions for correcting wavefront error upon removal of corneal tissue in accordance with the determined profile. A fill material to be used to fill space within the tissue volume upon the removal of corneal tissue is selected. An expansion factor is determined: $(Nc-1)/(Nm-Nc)$, wherein Nc and Nm are indices of refraction of cornea tissue and fill material, respectively. An expanded ablation volume in the cornea is determined as the determined profile with its thickness multiplied by the expansion factor. Cornea tissue is ablated according to the determined expanded ablation volume, and a stroma space vacated by ablated cornea tissue of the expanded ablation volume is filled with the fill material.

The expanding of the ablation volume may be along a direction of an optical path traversing the cornea. The method may further include converting an OPD wavefront error profile to an ablation cornea tissue volume using an index of refraction of the cornea, to account for an optical path length in cornea versus that in air, and transforming a cornea tissue volume according to the OPD profile at the apex of the cornea to the ablation cornea tissue volume inside the cornea.

The ablating of cornea tissue may include generating an excision line path. This may involve (i) generating a beam of laser pulses with pulse duration between 10 and 2000 femtoseconds, (ii) focusing the beam to an interaction point inside the cornea such that the laser pulses generate ablation spots with diameters ranging from 1 to 20 microns, and (iii) directing the beam by a computerized laser control unit, overlapping the ablation spots generated by the laser pulses by positioning the laser focus location at a separation in the range of 0.7 to 1.8 times an ablation spot radius. The ablating of cornea tissue may include controlling the generation of at least one excision line, and positioning the at least one excision line to overlap to another excision line to generate an excision plane, wherein an excised line separation ranges from 0.7 to 1.8 times an ablation spot radius.

The method may further include applying a monitoring measurement to the eye, and terminating the filling of the stroma space when the desired corneal profile is attained as determined by the monitoring measurement.

Another method is provided. This method is for reducing heating of the cornea during an intrastromal laser surgery. A corneal tissue volume profile to be ablated is determined. A cutting pattern for the tissue volume is determined including a series of cutting planes. Adjacent planes of cut are separated by greater than 0.7 times the radius of an ablation spot created by a single shot of laser pulses. In some embodiments, these separations may be limited to not more than 1.8 times the radius, while in other embodiments they may be more than 1.8 times the radius. The cut pattern is converted into executable steps in a computerized program for controlling a laser beam to cut the tissue volume. The laser beam is directed to cut the tissue volume into a plurality of pieces according to the cutting pattern.

Dissected tissue may be absorbed into the surrounding tissue and/or removed such as by suctioning the tissue from the cornea. For example, a cannula may be inserted and the suction applied thereto.

The stroma space vacated by ablated cornea tissue of the expanded ablation volume may be filled with fill material, while a monitoring measurement is applied to the eye. The filling of the stroma space may be terminated when the desired corneal profile is attained as determined by the monitoring measurement.

A method of LASIK, corneal, or intrastromal laser surgery is also provided. Excisions are made in a Bowman's layer of an eye, including ablating tissue in the Bowman's layer in accordance with an excision pattern. Tissue ablation is performed in a stroma located posterior to the Bowman's layer. In this way, an anterior stroma layer including the Bowman's layer with the excisions is made to conform to a shape of a stromal bed created by the tissue ablation. The excision pattern may include line or ring cuts or both.

A method of filling an ablated tissue volume in a stroma of an eye is also provided. An entry is created to cut an eye to provide for an entry point. A channel is excised, and an entry cut opening is connected to the ablated tissue volume. A cannula is inserted through the entry cut to the ablated volume, and a fill material is injected therein. A monitoring measurement may be applied to the eye, and the filling of the stroma space may be terminated when the desired corneal profile is attained as determined by the monitoring measurement.

A method is also provided for dissecting a cornea tissue volume inside a cornea. Laser pulses are generated that transmit through at least a portion of the cornea. The laser pulses are focused inside the cornea and at a region of tissue to be dissected. A three-dimensional cut pattern is determined to dissect the tissue volume. A laser pulse deposit pattern is calculated using single laser spot ablation profile. The laser spot deposit pattern is divided into a series of ablation planes using one or more layers of laser spots. The ablation planes include (i) at least one layer of contiguous laser spots, and (ii) at least one grid pattern of contiguous laser spots. The laser pulses are directed in accordance with the calculated pattern.

The ablation planes may be ordered starting from the farthest to the closest plane to the anterior cornea surface.

The laser may be directed to ablate tissue in accordance with the farthest ablation plane. The tissue ablation process is continued to the next ablation plane in the sequence, and repeated until the tissue volume is dissected in accordance with the cut pattern. The calculating may include overlapping focused laser pulses between 0.7 to 1.8 of the laser spot radius within the region of tissue to be dissected. Volumes of corneal tissue between lines of the grids of the adjacent layers are advantageously removed even though they are not directly ablated, thereby reducing heating of the cornea compared with a process of direct ablation of the entire removed corneal tissue volume.

One or more computer readable media having program code embodied therein for programming one or more processors to control any of the methods described herein.

DETAILED DESCRIPTION OF PREFERRED AND ALTERNATIVE EMBODIMENTS

The same inventor, Dr. Shui Lai, has disclosed previously in "Method of Making High Precision Optics Having a Wavefront Profile", at U.S. provisional patent application Ser. No. 60/820,340, filed Jul. 25, 2006, and contemporaneously-filed U.S. non-provisional application of the same title, serial number not yet known, a method of controlling an index of refraction in media across interfaces to improve accuracy of making such optics that have small amplitude profiles and that involve a high degree of accuracy and precision. The contents of those applications are incorporated by reference in their entirety.

In the present application, intrastromal ablation is achieved using a high precision laser. One example of such laser is a femtosecond laser manufactured by IntraLase, Irvine, Calif. In U.S. Pat. Nos. 5,984,916 and 6,325,792, Dr. Lai disclosed methods and devices of femtosecond laser corneal surgery. In U.S. Pat. No. 5,549,632, Dr. Lai disclosed an applanating device for improving accuracy of laser surgery. In U.S. Pat. Nos. 5,993,438, 5,984,916 and 6,325,792, methods of deposition of laser pulses to excise cornea tissue were disclosed. The contents of all of these issued patents are incorporated herein by reference in their entirety.

In the following description of embodiments, the term "ablation" of tissue is used to mean destruction of tissue using laser energy. In such process, tissue is generally transformed into smaller pieces having microscopic dimensions. The term "vaporized" is used to mean destruction by laser energy, e.g., of corneal tissue, and transformation into a vapor-like state. "Cut" is used to mean excision using a laser. "Ablation tissue volume" is used to mean a three dimensional volume of tissue that is intended to be ablated, or is being ablated in a described process and/or has been ablated. A tissue volume profile is used to mean the three dimensional profile of a volume of tissue. "Ablation cavity" is generally used interchangeably with tissue cavity. Ablation spot or laser spot is intended to mean the tissue cavity generated by a shot of one or more laser pulses at a location in a corneal tissue. "Cannula" is used to refer to a narrow tubular object having at least one opening at its distal end, which can be made of metal, plastic or other material and is suitable to carry fluid into or out of a stromal cavity in the cornea.

Intrastromal Laser Ablation of Corneal Tissue

Ablation of cornea tissue in accordance with one embodiment involves the following. A beam of laser pulses is generated with wavelengths transmitting through the corneal tissue, and pulse duration of 10 to 2000 femtoseconds. The laser beam is focused through a certain portion of the cornea to an interaction point inside the cornea such that each laser pulse generates an ablation spot or an ablation cavity with a diameter ranging from 1 to 20 microns. The laser beam is directed by a computerized laser control unit, overlapping the ablation spots generated by the laser pulses by positioning the laser focus location at a separation center to center, in a preferred range of 0.7 to 1.8 times the ablation spot radius. At this point, a laser generates a cut path, i.e., a path in which the cornea tissue is destroyed and is turned into small particles and vapor. Precise placement of each laser ablation spot in X Y and Z location inside the stroma may be made possible using an applanator device and method as disclosed in U.S. Pat. No. 5,549,632 by the same inventor, Dr. Shui Lai, which is incorporated here by reference.

To form an excision plane, a computer control unit is utilized in the generation of multiple excision lines that are positioned to overlap next to each other to generate an excision plane. The range of the line overlap is controlled by placing the line separation in the range of preferably more than 0.7 and less than 1.8 times the ablation spot radius, and preferably not less than 1. The excision lines may form a pattern of raster of substantially straight lines, one aligned with the next, or formed by a spiral while maintaining sufficient overlap between the spiral circles.

Wavefront Correction

Wavefront aberrations of an eye generally include both low order and the high order terms as expressed in Zernike polynomials. Low order aberrations including sphere, cylinder and axis can be described in the second order terms, and those aberrations described in the third and higher order terms are referred to as the high order aberrations.

The surgery may be divided into two treatment groups according to an extent of refractive correction required in a patient, and alternatively, by an amount of corneal tissue to be removed. In group one, highly precise surgical methods are described below to be utilized to controllably alter an optical path difference (OPD) of a high order wavefront error of an eye. In the second group, improvements for correct low order refractive errors that involve removal of larger amount of tissue volume are described below.

Correcting High Order Wavefront Errors and the Low Refractive Error Group

Even though a femtosecond laser is among the most precise intrastromal laser instruments currently used, any correspondingly or higher precision technology may be used as it may be developed, each of the laser pulses creates tissue destruction in the stroma tissue. The amount or the volume of the tissue destroyed is proportional to the energy content of the laser pulse. Using about one micro-joule or less and focusing into a volume of about two microns in diameter, the tissue volume destroyed is about two microns in diameter. However, the desired precision for a high order wavefront correction is generally less than two microns, and the RMS value of typical wavefront error is about one micron or less as measured in optical path difference (OPD), and that is about 0.73 microns of corneal tissue. Therefore, a femtosecond laser is not accurate enough to make a meaningful wavefront correction, except in cases of very distorted eyes. In the example above, a two micron ablation spot size, certain laser energy level in the range of one micro-joule, and laser focus spot size of 1-2 microns may be used. These parameters are used for illustrative purpose. Other ablation spot dimension or laser energy content or focus spot size may be used without affecting the benefits of the proposed device and method.

Likewise for cases of refractive errors of less than one diopter in sphere or cylinder, one may have difficulty to achieve accurate laser ablation to satisfy the profile requirement. Using the Munnerlyn formula, for each diopter of myopic correction, a tissue lens with about twelve microns of tissue at the center of lens tissue and tapered to zero at a six mm diameter zone edge, is to be removed. Accuracy may be compromised, with an ablation accuracy of about two microns with the current femtosecond laser, which is substantially less accurate than that of an excimer laser ablation which is about 0.25 microns per laser pulse.

Figure 1A:
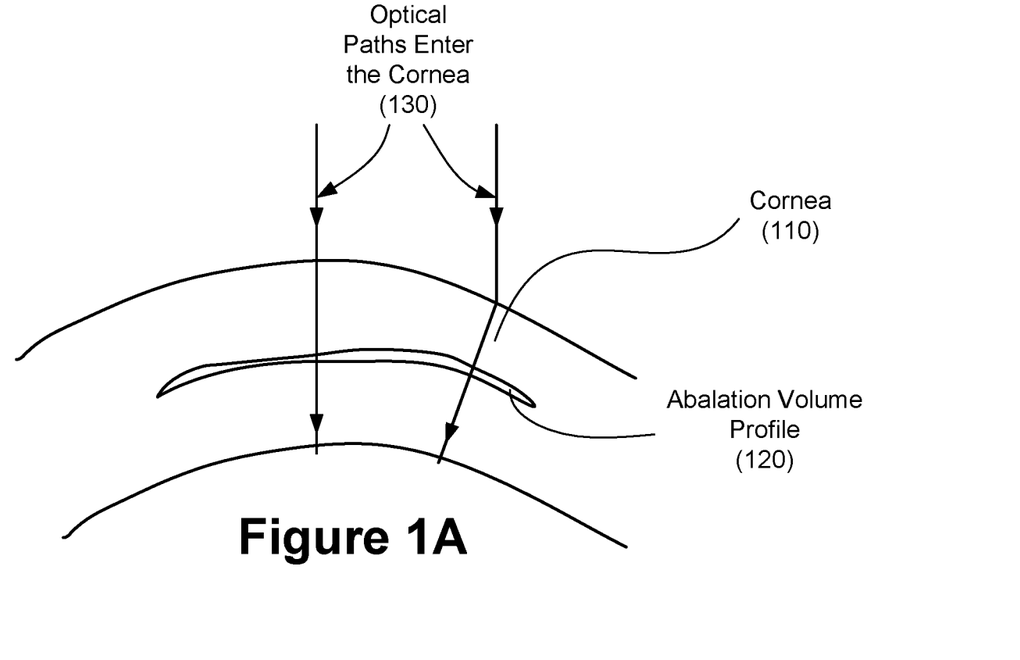
FIG. 1A illustrates a cross-sectional side view of an ablation volume profile within a cornea.

In an embodiment, an intrastromal volume and its three dimensional shape to be ablated are first determined. An example is illustrated schematically in FIG. 1(a), showing a cross-sectional view of a cornea 110 and an ablation volume profile 120, as well as optical paths entering the cornea 130. The wavefront error is measured using either a subjective and/or an objective wavefront aberrometer or wavefront refraction instrument, for example as disclosed in "Subjective Refraction Method and Device for Correcting Low and Higher Order Aberrations", which is U.S. Ser. No. 11/675,079, filed Feb. 14, 2007 and U.S. Ser. No. 60/773,758, filed Feb. 14, 2006, and in "Subjective Wavefront Refraction Using Continuously Adjustable Wave plates of Zernike Function", which is U.S. Ser. No. 11/746,051, filed May 8, 2007 and U.S. Ser. No. 60/746,772, filed May 8, 2006, by the same inventor, Dr. Shui Lai. These applications are hereby incorporated here by reference.

A three dimensional corneal tissue volume is constructed based on an OPD profile, and the index of refraction of the cornea tissue. Using a method in accordance with a preferred embodiment and/or as disclosed in the 60/820,340 application incorporated by reference above, one may perform intrastromal ablation to induce small OPD changes using a substantially larger or expanded tissue ablation than one could have done with a traditional direct corneal tissue removal method, using the method of replacing the evaporated tissue with a fill material having closely matched index of refraction to that of the cornea. Additionally, one selects a material that is suitable to be inserted in the stroma, which is selected for its properties of bio-compatibility with cornea collagen and has good nutrient diffusion characteristics to maintain a healthy cornea. Silicon hydrogel is a good candidate; and its bio-compatibility has been validated in corneal implant studies. Silicon hydrogel is used in commercial soft contact lenses. The index of refraction of the selected implant material is determined; and its value is typically larger than that of the cornea which is about 1.376. Using a method in accordance with a preferred embodiment, one can now calculate the "expanded" corneal tissue volume. The expansion factor is determined preferably by:

$$\text{Expansion factor}=(Nc-1)/(Nm-Nc), \quad (1)$$

where Nc and Nm are the index of refraction of the cornea and the implant material, respectively.

Figure 1B:
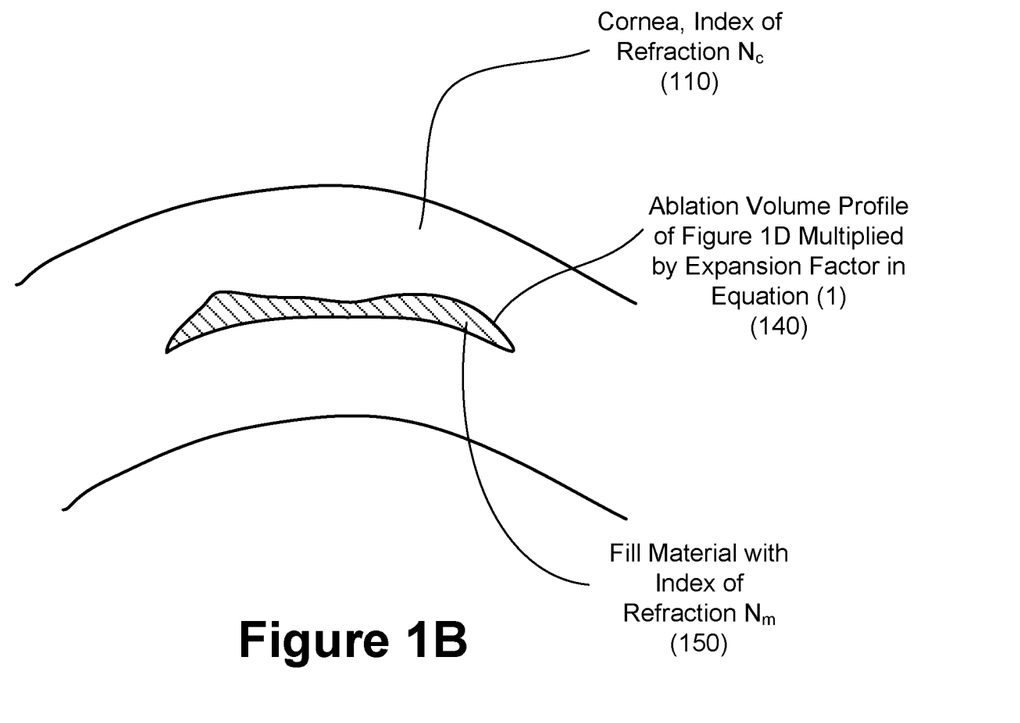
FIG. 1B illustrates a cross-sectional side view of an expanded ablation volume profile within a cornea having refractive index Nc filled with fill material of refractive index Nm.

Referring now to FIG. 1(b), an expanded stroma ablation profile 140 is determined by multiplying the corneal tissue profile with the expansion factor. The ablation profile 140 in one of the three dimensions is expanded by the expansion factor in Equation (1) along the direction of the light ray, the thickness dimension of the ablation tissue volume, which is illustrated as reference element 130 in FIG. 1(A), and as 190 in FIGS. 1(e) and (f) Fill material 150 with index of refraction Nm is provided to fill the volume 140 vacated by corneal tissue upon ablation.

Since the wavefront error of the eye is being corrected, the ablation tissue volume profile 140 is determined by the OPD of the eye. Therefore, a height of tissue volume is measured along the direction of the light path 130 traversing the cornea 110 as shown in FIG. 1(a). The light ray is normal to the cornea 110 at the center, and is tilted against the cornea 110 normal as it is farther away from the center. This concept is elaborated in further detail with reference to FIGS. 1(c) through (f).

Figure 1C:
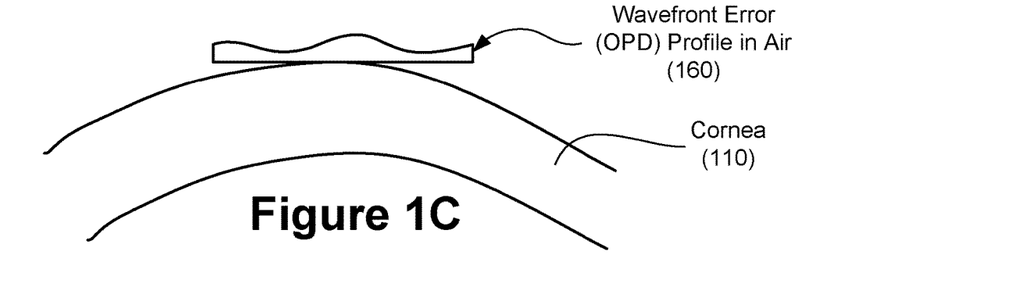
FIG. 1C illustrates a wavefront error OPD profile in air.

In FIG. 1(c), an example of a high order wavefront profile 160 is shown. The OPD of the wavefront error is defined as optical path error at the corneal apex. As a light ray enters the eye, the ray is refracted at the cornea surface. In one embodiment, the accuracy of tissue ablation to correct OPD wavefront error is improved. The ablation tissue volume is determined taking into account the refracted optical ray path in the cornea.

Figure 1D:
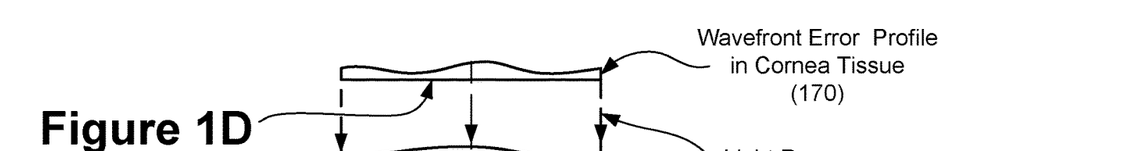
FIG. 1D illustrates the wavefront error profile in cornea tissue.
Figure 1E:
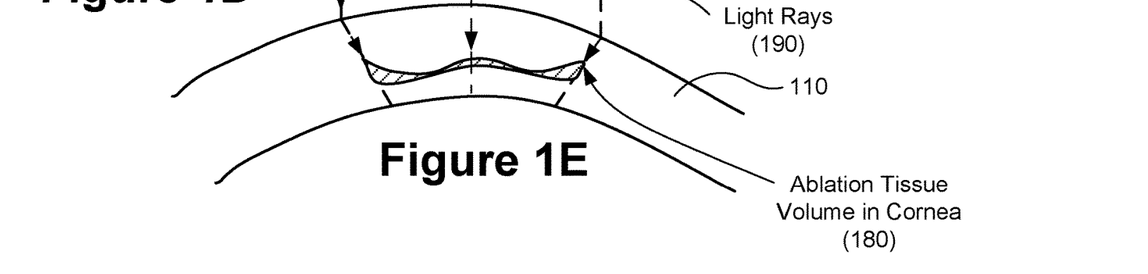
FIG. 1E illustrates a cross-sectional side view of an ablation tissue volume in cornea.
Figure 1F:
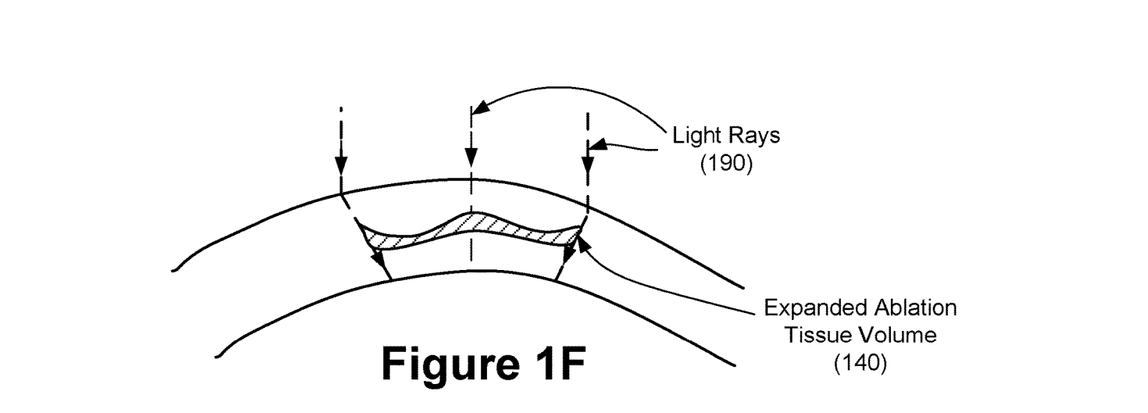
FIG. 1F illustrates a cross-sectional side view of an expanded ablation tissue volume in cornea.

The wavefront error profile in air 160 having an index of refraction of approximately 1.0 is first converted to a wavefront error profile in corneal tissue 170 having an index of refraction of the cornea, or approximately 1.376. The height of the wavefront profile is reduced across the entire x/y plane by a factor of 1/corneal refractive index, as illustrated in FIG. 1(d). Next the ablation volume in FIG. 1(d) is configured inside the cornea, and modified in shape to the ablation tissue volume 180 that accounts for the optical path traversing the cornea 110 as illustrated in FIG. 1(e). Now, using the expansion factor method above, the tissue volume 180 in the cornea according to the illustration of FIG. 1(e) is multiplied by the expansion factor along the direction of the optical ray 190 to obtain an expanded ablation tissue volume 140 as illustrated in FIG. 1(f). Note that the original wavefront profile 160 has a vertical perimeter (vertical edge), and the expanded ablation tissue profile 140 has a tilted perimeter, but along the direction of the optical path in the cornea.

For example, if the implant material has an index of 1.443, the expansion factor is 5.6 using Equation (1). The height of the tissue volume along the light ray's traversing direction is multiplied by the expansion factor of 5.6.

From another perspective, the example above provides for an improvement in the accuracy of the intrastromal ablation by a factor 5.6. One can achieve even greater improvement, by selecting an implant material having index of refraction more closely matched with that of the cornea. In other words, the limit of the femtosecond laser ablation accuracy of 2 microns is effectively reduced to 0.35 microns (2 microns/5.6), approaching that of an excimer laser.

Correcting Larger Diopter Power Refractive Errors

For a correction of 4 diopters myopia, with a 6 mm optical zone diameter, the estimate ablated tissue thickness is about 48 microns at the center of the tissue lens without tissue expansion. If the tissue profile is to be expanded, the ablation volume would increase to over 300 microns in corneal thickness (using the example of an expansion factor of 5.6 or above). The removal of such thick cornea tissue may endanger the mechanical stability of the globe. An expansion factor method that is useful for performing small and thin ablation tissue volumes is not as useful for correcting higher diopter, low order refractive errors. Direct tissue ablation of the tissue profile can be used, notwithstanding some un-desirable effects as disclosed in the following. As it is recognized in the present invention, there are several problems associated with a direct tissue removal method when a conventional method of tissue removal is used.

First, the heat released from each laser pulse is kept inside the stroma layer, as compared to surface ablation of PRK or LASIK where the heating is lower in the process and any remaining heat is dissipated to the air immediately next to the ablation sites. The heat problem is worse in an intrastromal ablation; because tissue breakdown is mediated through a photodisruption. The threshold level of a photodisruption is much higher than that of UV absorption in the case of an excimer laser ablation process. More residual energy is released in an intrastromal ablation process. Coupling the extra heat released and the heat trapped inside the stroma, a temperature rise is correspondingly higher. This is particularly harmful to corneal health. A solution to reduce the trapped heat in a intrastromal ablation is provided below.

Method to Lower the Heat Trapped in Cornea

A conventional tissue removal process is described at U.S. Pat. No. 5,993,438, which is hereby incorporated by reference. The laser parameters and ablation characteristics may be as described earlier: the tissue volume of about 2 microns in diameter ablation spot (tissue cavity) is created at the laser's focal point. The laser pulse is then moved to its next intended location and creates the next tissue cavity. In order to make an excision or tissue cut, these cavities are arranged to overlap, and particularly the centers of the cavities are separated by less than the cavity diameter, for example, 1.5 micron separation for 2 micron cavities. A series of laser pulses creates a cut path. Cut paths are created and positioned again overlapping such that stromal tissue in a defined volume is eventually totally vaporized.

Figure 2:
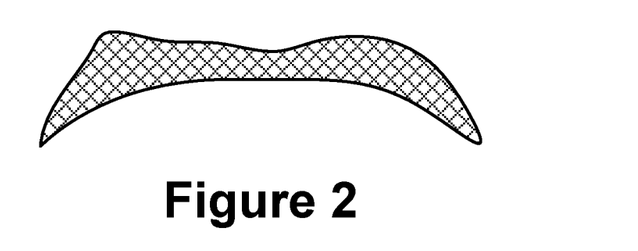
FIG. 2 illustrates a cross-sectional side view of a cross sectional side view of an ablation tissue volume.

To reduce the amount of trapped heat, one may use the laser to dissect the tissue into small pieces of less than certain dimensions, for example, in the range of 5 microns to 50 microns in size. An illustration of a dissected ablation volume is shown in FIG. 2. The dissected tissue shape can be a cube, parallelepiped, or other less regular shape. The exact shape and dimensions of the dissected tissue are not limiting factors. The preferred shape requirements are set forth below. As an example for illustration purposes, the laser parameters are selected such that the ablation cavity of each focused laser pulse created is about 2 microns in diameter. In an embodiment, instead of placing the adjacent excision planes at the overlapping at center to center separation distance of 1.5 microns (or 1.5 times the ablation spot radius), one places the next intrastromal excision plane at 10 microns apart as an example. Thereby, more tissue volume is not vaporized than those vaporized in the excision process. Therefore, we reduce the laser energy in each of x/y/z directions by a factor of 7 (10 microns/1.5 microns). In this example, when the laser dicing is completed, we have multiple cornea tissue cubes of approximately 8 microns. The reduction of laser energy is by $1/7$ (cutting one plane instead of 7) to the power of 3 (for the 3 dimensions), or advantageously reduced by about $1/342$ times. Hence the safety of the intrastromal surgery and the preservation of the corneal health are significantly improved.

Figure 7:
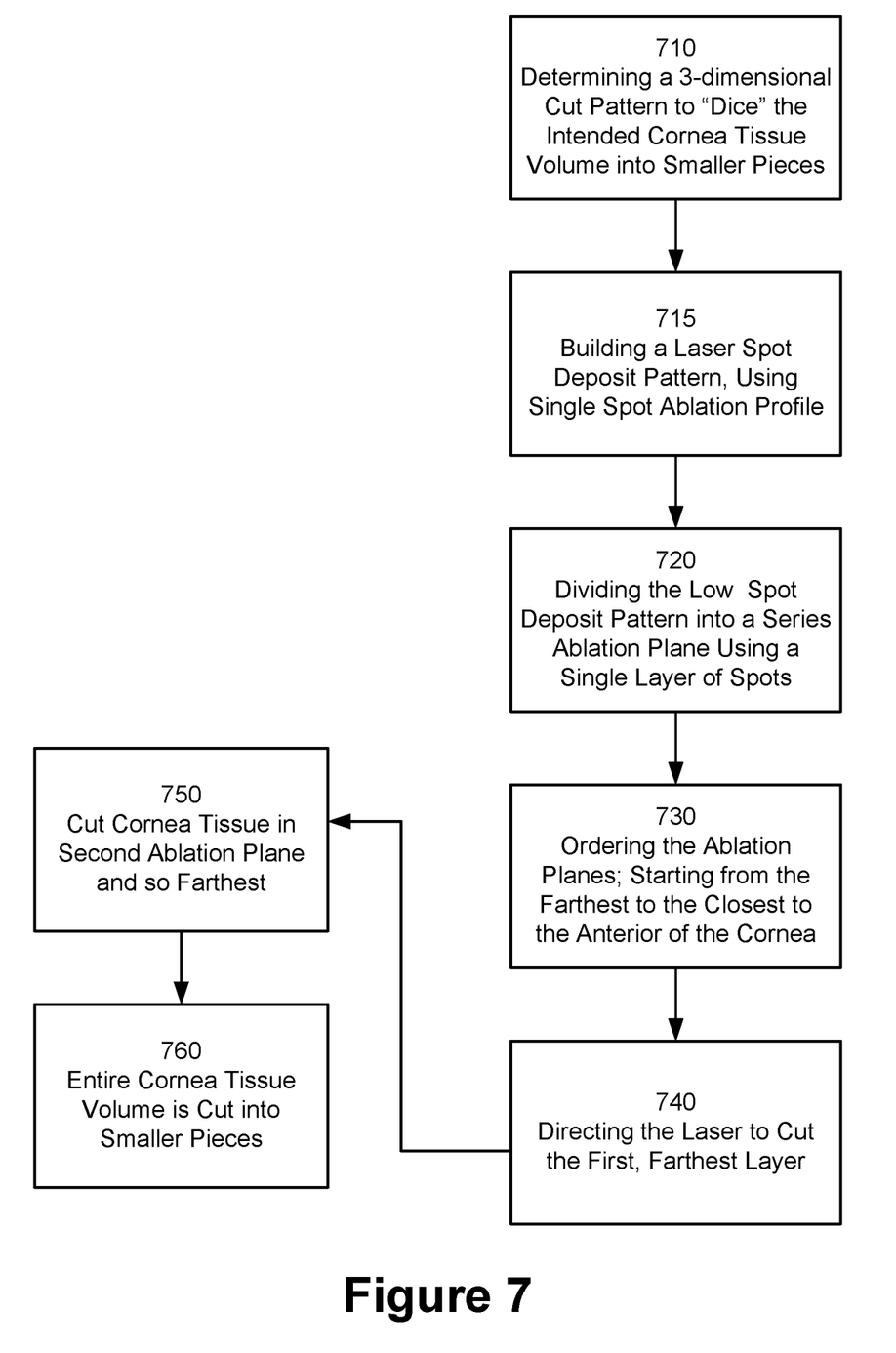
FIG. 7 is a flow chart illustrating a method of dissecting cornea tissue.

Another embodiment for dissecting the cornea tissue in smaller pieces is provided herein. It is recognized that intrastromal ablation process prefers a clear transmitting cornea to avoid scattering, or diffusion of the cutting laser beam and thereby loss of its cutting effectiveness. One method to avoid beam interference with the cut lines in the cornea is to perform the cutting from bottom up, or "inside out". A computer with one or more programming media controls the positioning and the focusing of the cutting laser beam. As illustrated in FIG. 7, a three-dimensional cut pattern is first determined to dissect an intended tissue volume into small pieces 710, also illustrated by the hatched patterns in FIG. 2 and FIGS. 3A and 3B. In 715, a laser spot deposit pattern is generated based on a laser spot ablation tissue removal profile. The three-dimensional laser spot cut pattern is divided into a series of ablation planes, wherein each one has the thickness or the height of about the overlapping distance of tissue ablation, using a single layer of laser pulses, 720. The series of ablation planes is ordered in 730 in an ablation sequence from the farthest to the nearest to the anterior surface to the cornea. The laser beam is then directed by a scanning mechanism, and focusing optics serve to position the cutting point to excise the first ablation plane in the ordered sequence, which is farthest away from the anterior surface of the cornea, or the bottom layer 740. After the first farthest plane is excised, the cutting process moves to cut the second farthest plane 750, and so forth, until the entire cut pattern is completed 760. In this process, the laser beam may be shut off when it is being scanned across a region where the tissue is not to be ablated. The cut pattern is preferably generated with the laser ablation spot layer by layer from bottom up.

Figure 8A:
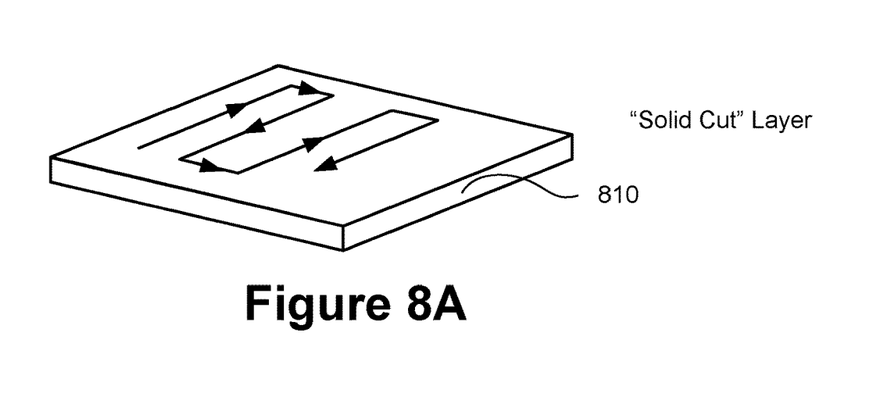
FIG. 8A illustrates a solid layer cut in a method of dissecting cornea tissue.
Figure 8B:
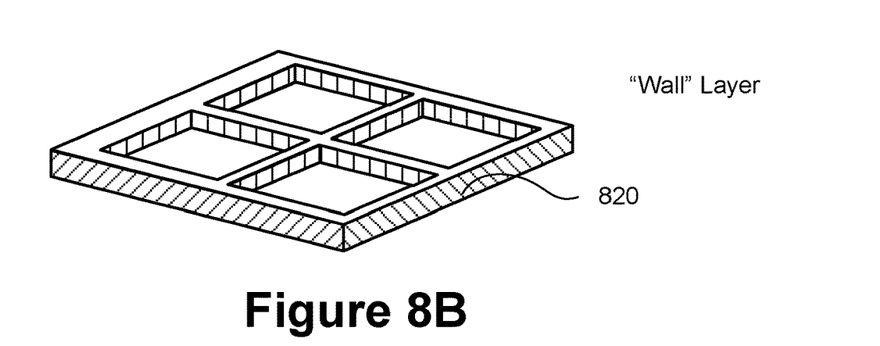
FIG. 8B illustrates a wall layer or grid line cut adjacent the solid layer cut of FIG. 8A.
Figure 8C:
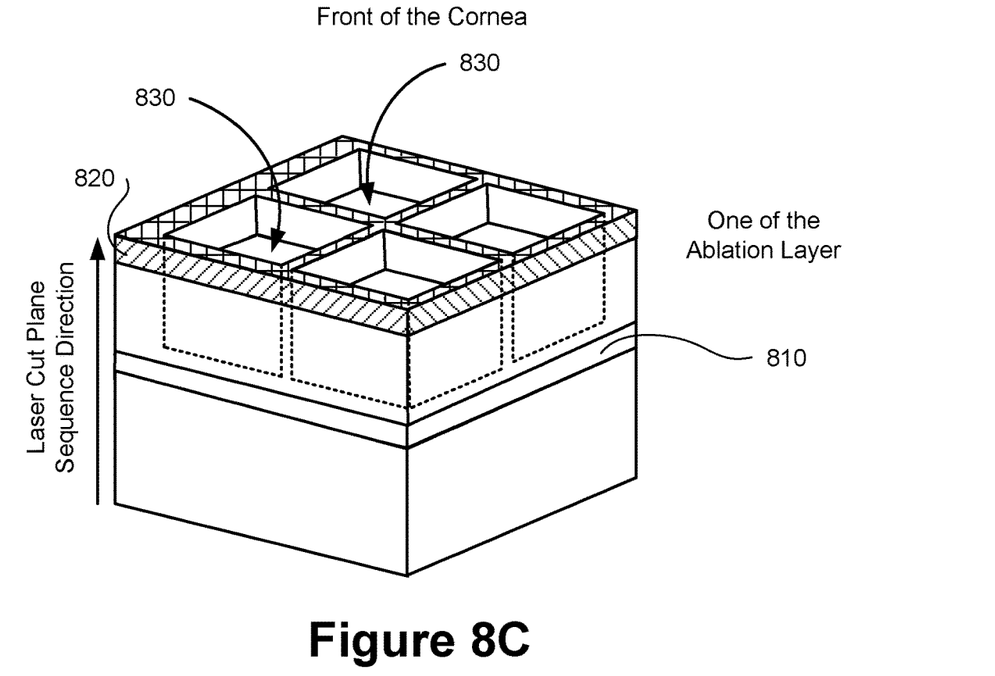
FIG. 8C illustrates a view of the overall cut process beginning with FIG. 8A, and multiple iterations of wall layer cuts according to FIG. 8B.
Figure 8D:
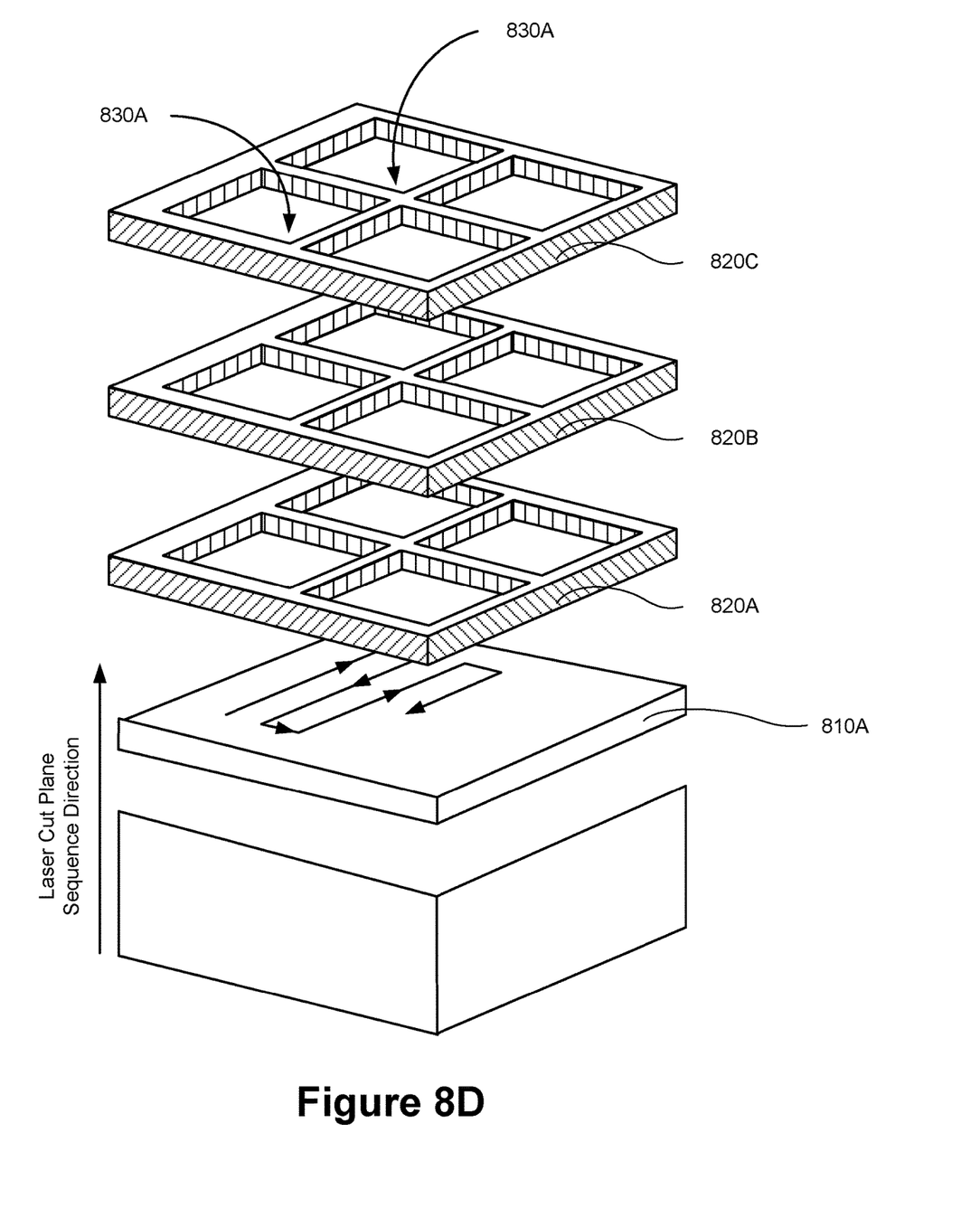
FIG. 8D is an exploded view illustrating consecutive layer cuts according to the methods of FIGS. 7 and 8A-8C.

FIGS. 8A, 8B, 8C and 8D schematically illustrate an exemplary process of an intrastromal ablation including cutting the cornea into small pieces, which has the advantage of reduced heating compared with a process wherein all of the tissue in a corneal volume is directly ablated. First, the laser is directed to the farthest layer 810 from the anterior cornea. In the example of FIG. 8A, a solid layer of cornea tissue is initially ablated. During this process, the laser pulses are positioned to overlap to fill a solid ablation layer. A next layer 820 is illustrated in FIG. 8B. Here the laser only ablates the "wall" surrounding the "dissected" tissue like a grid. The next ablation plane moves up closer to the anterior cornea surface. The next ablation layer is the same or similar to that shown in FIG. 8B layer. The ablation repeats for as further layers to cut out the "wall cut" layer pattern, until the height of the un-ablated tissue "cubes" 830 reaches a certain height as predetermined by a computer program which controls the process. Then, another solid cut layer like FIG. 8A may be then ablated to separate the cube from the rest of the tissue. This process is repeated until an entire, selected three-dimensional tissue volume is dissected into smaller pieces. FIG. 8C illustrates the overall process of ablating beginning with layer 810, and successive layers 820 building cubes 830 or other polyhedrons 830. The shape of the dissected tissue pieces may in other shape in addition to cubes, round, triangular, parallelepipeds, hexagons or any regular or irregular shapes. FIG. 8D illustrates an exploded view of an initial solid cut layer 810, followed by wall or grid cuts of layers 820A, 820B, 820C and so on, leaving polyhedrons 830A of corneal tissue that is not ablated directly by the laser.

Figure 3A:
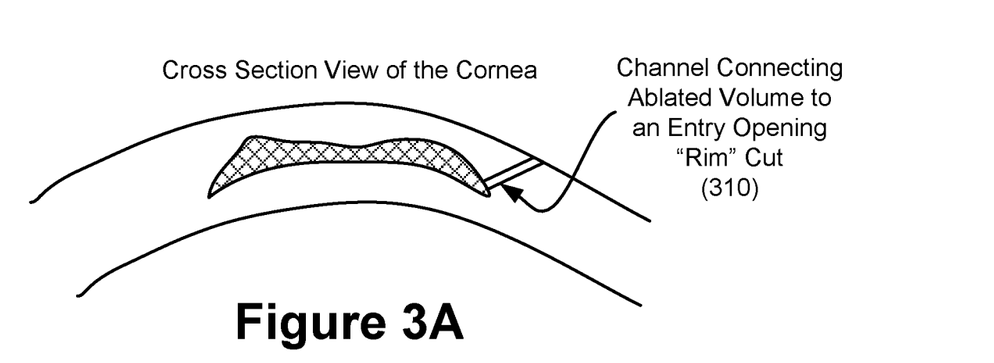
FIG. 3A illustrates a cross-sectional side view of a cornea with an ablation tissue volume and channel connecting to entry opening rim cut.
Figure 3B:
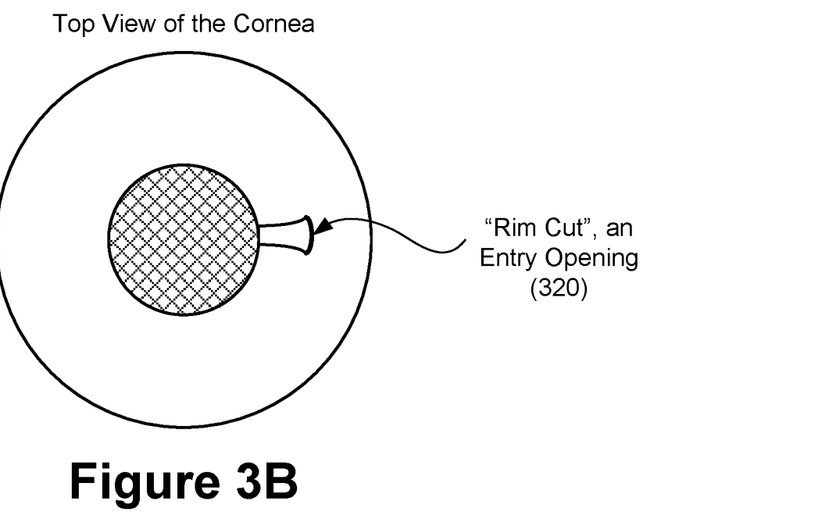
FIG. 3B illustrates a front view of a cornea with an ablation tissue volume and channel connecting to entry opening rim cut.

To remove the dissected tissue, a channel 310 is shown in FIG. 3A connecting to an entry opening or a "rim" cut 320 of an arc length of 1 mm or less at the 6 mm zone edge, or further outside the zone, as illustrated in FIG. 3B. No limit is imposed on the shape of the "rim" cut, 320 which can be straight, or curved. The length of the cut 320 is preferably small, but sufficient in size to allow insertion of a cannula as described below. A channel 310 is excised connecting the volume of the dissected tissue to the arcuate cut as shown in FIG. 3A. The cut opening provides for an entry point for a cannula, inserting into the volume of dissected tissue and suctioning out the dissected tissue. The cannula has at least one opening at its distal end, with a size of 40-200 microns. The dissected tissue can be made to be larger or smaller, as long as the dissected tissue can be suctioned through the cannula opening.

A second problem of correcting high degrees of refractive error using the traditional tissue ablation method is that after the tissue volume is totally ablated, water is vaporized, and the hot tissue fragments remain. It will typically take about 30 minutes or longer while the vaporized tissue is absorbed through the stroma. The suction method clears out the vapor and the hot tissue remains. It provides the benefit of not having to wait for 30 minutes, which lengthens surgery time, and interrupts the flow of the surgery.

Alternatively, one may lower the heat trapped and without suctioning out the dissected corneal tissue, by placing the cutting plane separation to about 1.8 to about 4 times the ablation spot radius, in our 2 micron spot size example. In one embodiment, the remaining tissue after cutting is in the size of about 0.3 to 2 microns, which is then left to be absorbed by the surrounding tissue. In this case, there is still improvement in reducing the heat as compared to the case of total ablation of all tissue, and one has to wait for the remaining tissue pieces to be absorbed. However, it has the advantage of not having to be suctioned out. The exact cutting plane separation in this embodiment is not a limiting factor. It can be adjusted to any value for so long as the remaining tissue can be absorbed.

Embodiment to Conform Anterior Stromal Tissue to the Stromal Bed

After a significant amount of stromal tissue is removed, one expects the anterior portion of the cornea over the ablated tissue volume would collapse, and thereby accomplish a corneal shape change. However, the anterior stroma layer includes a crusty (semi-firm) layer, the Bowman's layer. It possesses a certain degree of mechanical rigidity. Therefore, the collapsing of the anterior stromal layer is expected to be partial, not totally conforming to the stromal bed created after the intended tissue volume is vacated. This undermines the accuracy of the intended surgical outcome, and affects the healing process.

In an advantageous embodiment herein, one applies the intrastromal laser to excise the Bowman's layer to its full thickness of about 40-50 microns, to cut the Bowman's "shell" into regions to relax the mechanical rigidity of the shell structure so that it conforms more readily to the stromal bed.

Figure 4:
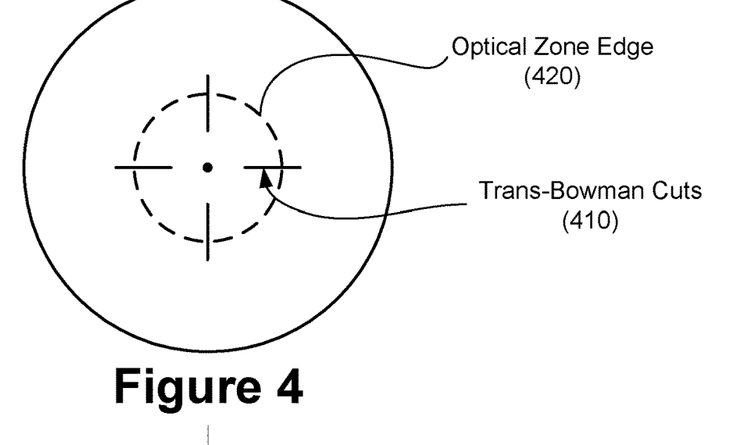
FIG. 4 illustrates a cornea having trans-Bowman cuts and an optical zone edge.

FIG. 4 illustrates four radial trans-Bowman cuts 410 (cut that is through the majority or the entire thickness of the Bowman's layer), starting from 3-4 mm diameter out to 6-7 mm. Six, eight or more cuts are also applicable. An optical zone edge 420 is also shown in FIG. 4.

Figure 5:
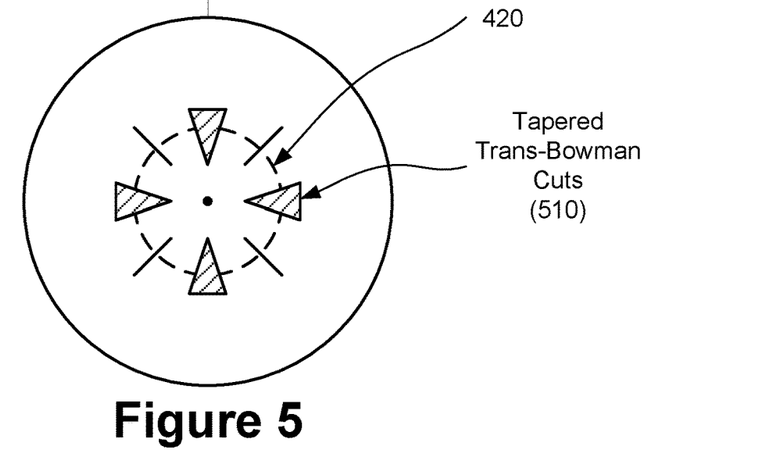
FIG. 5 illustrates a cornea having the trans-Bowman cuts of FIG. 4 and tapered trans-Bowman cuts.

FIG. 5 shows an eight cut pattern with an alternating cut length including tapered trans-Bowman cuts 510 as well as four radial trans-Bowman cuts 410. In this embodiment, the cuts 510 have tapered shapes, such that the method may include removing more Bowman tissue as it is closer to the outer zone boundary. This allows for more contraction of the Bowman layer near the periphery of the optical zone 420. The starting location of the trans-Bowman cuts, the length, or the width of the cuts are examples and they are not the limiting factors. Cuts through partial thickness of the Bowman layer may also be used for the mentioned purposes.

Figure 6:
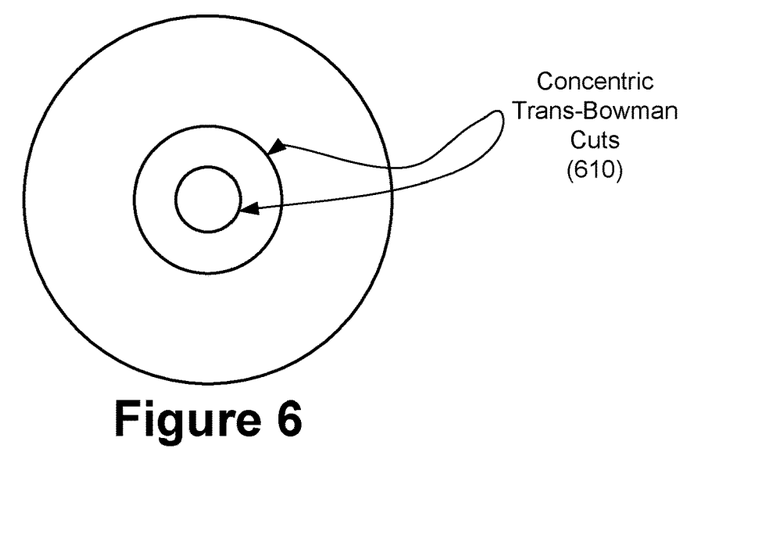
FIG. 6 illustrates a cornea having concentric trans-Bowman cuts.

FIG. 6 schematically illustrates two trans-Bowman concentric ring cuts 610. No limitation is implied here regarding the number of ring cuts, lengths or the widths of the cuts, the placement of the cuts, or mixing of various cut patterns in the examples, or arranging the cuts in certain patterns, or the cutting sequence.

The present embodiment of relaxing the Bowman's layer may be applied not only to intrastromal surgery, but also to LASIK and other corneal surgeries to relax the Bowman layer rigidity to achieve a more desirable surgical outcome.

Filling the Intrastromal Volume

For the first treatment group, where the ablation profile is expanded using an index matching method, after the tissue is removed, the selected material in liquid form is injected through the arcuate cut opening to the ablated tissue space as illustrated in FIG. 3A. Measurements by a corneal topographer (e.g., manufactured by Carl Zeiss Medditec) or a wavefront aberrometer (e.g., manufactured by Wavefront Sciences) may then be applied to monitor the front surface profile of the cornea. When the intended cornea topography or wavefront map is attained, the injection is stopped and UV light is applied to polymerize the material into hydrogel.

The cannula may be attached through a tubing to a container of the liquid material. Furthermore, the cannula may be mounted in a fixture, which is fixed to the patient's head to immobilize any cannula or transfer tube movement, thereby reducing distortion of the cornea that it may cause.

The present invention is not limited to the embodiments described above herein, which may be amended or modified without departing from the scope of the present invention as set forth in the appended claims, and structural and functional equivalents thereof.

In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, all references cited above herein, in addition to the background and summary of the invention sections, as well as U.S. patent applications Ser. Nos. 60/826,043, 60/820,340, 60/804,919, Ser. Nos. 11/746,051, 11/764,160 and 11/675,079, and U.S. Pat. Nos. 7,220,255, 7,217,375, 6,761,454 and 6,836,371, also by Dr. Shui Lai, are all hereby incorporated by reference into the detailed description of the preferred embodiments as disclosing alternative embodiments and components.

I claim:

1. An apparatus for correcting wavefront aberrations of an eye using intrastromal laser surgery, comprising:
   (a) a laser;
   (b) a processor; and
   (c) one or more non-transitory computer-readable media having code embedded therein for programming the processor to control the laser to perform a method of dissecting a cornea tissue volume inside a cornea, wherein the method comprises:
      (i) determining a corneal ablation tissue volume profile for an eye in three dimensions for correcting wavefront error upon removal of corneal tissue in accordance with said determined profile,
      (ii) selecting a fill material to be used to fill a stroma space within the tissue volume upon said removal of corneal tissue,
      (iii) determining an expansion factor: (Nc−1)/(Nm−Nc), wherein Nc and Nm are indices of refraction of cornea tissue and the fill material, respectively;
      (iv) determining an expanded ablation volume in the cornea, wherein the expanded ablation volume comprises the determined profile with its thickness multiplied by said expansion factor in (iii); and
      (v) ablating cornea tissue according to the determined expanded ablation volume.

2. The apparatus of claim 1, further comprising a cannula coupled to a container of the fill material for filling the stroma space vacated by ablated cornea tissue according to the expanded ablation volume with the fill material.

3. The apparatus of claim 1, wherein the expanding of the ablation volume is along a direction of an optical path traversing the cornea.

4. The apparatus of claim 1, wherein the method further comprises (vi) determining the expanded ablation volume including:
   (i) converting an OPD wavefront error profile of the eye in air to an ablation cornea tissue volume using an index of refraction of the cornea, to account for an optical path length in cornea versus that in air, and
   (ii) converting the ablation cornea tissue volume to an expanded fill tissue volume to be filled by the selected fill material, and
   (iii) wherein the converting into fill tissue volume includes taking into account of the index of refraction of the selected fill material versus that in cornea.

5. The apparatus of claim 1, wherein aberrations of the eye to be corrected comprise:
   (i) one or more low order aberrations including sphere or astigmatism, or both; or
   (ii) one or more high order aberrations that are describable using Zernike polynomials of third and higher orders; or
   (iii) combinations of (i) and (ii).

6. The apparatus of claim 1, wherein ablating cornea tissue comprises generating an excision line path.

7. The apparatus of claim 6, wherein generating an excision line path comprises:
   generating a beam of laser pulses with pulse duration between 10 and 2000 femtoseconds,
   focusing the beam to an interaction point inside the cornea such that the laser pulses generate ablation spots with diameters ranging from 1 to 20 microns, and
   directing the beam by a computerized laser control unit, overlapping the ablation spots generated by the laser pulses by positioning the laser focus location at a separation in the range of 0.7 to 1.8 times an ablation spot radius.

8. The apparatus of claim 6, wherein ablating cornea tissue further comprises controlling the generation of at least one excision line, and positioning said at least one excision line to overlap to another excision line to generate an excision plane, wherein an excised line separation ranges from 0.7 to 1.8 times an ablation spot radius.

9. The apparatus of claim 1, further comprising a monitoring instrument configured to monitor the filling of the stroma space and terminate the filling of the stroma space when a desired corneal profile has been attained.

10. The apparatus of claim 1, further comprising an instrument for creating an entry cut opening to the eye to provide for an entry point, excising a channel, and connecting an entry cut opening to the ablated tissue volume.

11. The apparatus of claim 10, further comprising a cannula coupled to a container of fill material for injecting fill material through the entry cut to the ablated tissue volume.

12. The apparatus of claim 11, further comprising a monitoring instrument configured to monitor the filling of the stroma space and terminate the filling of the stroma space when a desired corneal profile has been attained.

* * * * *